United States Patent [19]

Handlos

[11] Patent Number: 5,298,012
[45] Date of Patent: Mar. 29, 1994

[54] TENDON GRAFT PREPARATION WORKSTATION

[75] Inventor: Kurt E. Handlos, Crestline, Calif.

[73] Assignee: Baxter International Inc., Deerfield, Ill.

[21] Appl. No.: 7,046

[22] Filed: Jan. 21, 1993

Related U.S. Application Data

[63] Continuation of Ser. No. 768,492, Sep. 30, 1991, abandoned.

[51] Int. Cl.$^5$ .......................................... A61B 19/00
[52] U.S. Cl. ........................................ 600/36; 606/1; 606/148; 69/19; 269/45
[58] Field of Search ............... 606/1, 57, 148; 600/36; 69/1.5, 19, 19.3; 24/68 D; 269/71, 45

[56] References Cited

U.S. PATENT DOCUMENTS

| | | | |
|---|---|---|---|
| 359,376 | 3/1887 | Ballou | 269/71 |
| 1,306,858 | 6/1919 | Salter | 269/45 |
| 1,334,971 | 3/1920 | Shore | 269/71 |
| 1,386,318 | 8/1921 | Cowan | 269/71 |
| 1,670,253 | 5/1928 | Gilbert et al. | 269/45 |
| 2,459,080 | 1/1949 | Killius | 269/71 |
| 3,743,904 | 7/1973 | Wiesler et al. | 318/162 |
| 4,013,281 | 3/1977 | Tokunaga | 269/61 |
| 4,183,511 | 1/1980 | Marek | 269/71 |
| 4,203,231 | 5/1980 | Van Note | 35/20 |
| 4,232,659 | 11/1980 | Dale | 600/36 |
| 4,466,601 | 8/1984 | Raines | 269/79 |
| 4,848,368 | 7/1989 | Kronner | 606/57 |
| 4,911,418 | 3/1990 | Dennis | 269/71 |
| 4,957,495 | 9/1990 | Kluger | 606/57 |

FOREIGN PATENT DOCUMENTS

0322191  11/1971  U.S.S.R. .................. 606/57

Primary Examiner—Stephen C. Pellegrino
Assistant Examiner—Jeffrey A. Schmidt
Attorney, Agent, or Firm—Kay H. P. Hannafan; Paul C. Flattery

[57] ABSTRACT

A device for holding a tendon graft in position as the tendon is scraped and sutured is described. The device includes a pair of tension arms that can be moved in both a horizontal and vertical plane. Horizontal movement of the tension arms can be used to adjust the amount of tension that is applied to a tendon graft. Vertical movement of the tension arms can be used to position the tendon graft in a location which enables medical personnel to more easily suture parallel lengths of a graft together.

22 Claims, 6 Drawing Sheets

TENDON GRAFT PREPARATION WORKSTATION

This is a continuation of application Ser. No. 07/768,492, filed on Sep. 30, 1991, now abandoned.

FIELD OF THE INVENTION

The invention relates generally to devices for holding tendon grafts and relates more specifically to devices for holding tendon grafts when such grafts are being scraped and sutured prior to re-implantation into a patient.

BACKGROUND OF THE INVENTION

In certain orthopaedic reconstruction procedures such as a semitendinosus gracilis composite graft procedure, it is necessary to remove a piece of tendon from a patient's knee area. After the tendon has been removed, it is frequently used to replace either the anterior or posterior cruciate ligament. These tendons and ligaments are illustrated in FIG. 1. The semitendinousus gracilis composite graft is illustrated as element 12, and a mid-third patellar tendon graft is illustrated as element 14. The anterior and posterior ligaments are illustrated as elements 16 and 18. Replacement of a ligament with a tendon 20 is illustrated in FIG. 2.

The anterior and posterior ligaments, 16 and 18, are generally much stronger than the tendons that are used to replace these ligaments. Therefore, when a substitute tendon is used, it may be necessary to double, triple, or even quadruple the thickness of a tendon graft to produce a replacement graft having a strength that is similar to the anterior or posterior ligament it is intended to replace. Therefore, in some surgical procedures, after a tendon graft has been harvested, a surgeon will loop the graft and suture opposing lengths 24 and 26 of the graft together as illustrated in FIG. 3. In many surgical procedures, two tendon grafts are looped together to form four strands of tendons which are sutured together.

Generally, it is desirable to suture such strands together on both an upper and a lower side of the strands. Therefore, after a surgeon will typically rotate the strands 180 degrees and suture the under side of the strands together. In the past, a surgeon has performed this procedure of suturing the strands together on a simple table or in mid-air. Since such strands are not under tension when they are sutured together, irregularities in the suturing may occur which can cause an unevenness in the loops. This unevenness may be intensified when the loops are rotated 180 degrees for suturing on the underside.

Therefore, a need existed to provide a device for tensioning such strands in a fixed, looped position to evenly stretch such strands before and during suturing. A need also existed to provide a device which could rotate such strands 180 degrees for suturing on the underside without changing the tension applied to the strands.

Another aspect of the surgical procedures in which tendon grafts are harvested is that the grafts generally need to be scraped prior to suturing or reinsertion into a patient. Generally, a harvested tendon graft will contain a certain amount of "meaty" tissue which needs to be scraped from the surface of the graft. In the past, a harvested graft was typically placed on a sterile cloth or disposable paper towel to scrape this tissue from the graft. One disadvantage of placing the graft on a flexible cloth or towel was that the cloth or towel had a tendency to slip and wrinkle while the graft was being scraped. Therefore, a need existed to provide a rigid, non-skid, sterile surface which could be used for supporting a graft as it is being scraped.

Yet another aspect of such surgical procedures is that after a tendon graft has been scraped and sutured, the graft is generally stored temporarily while the patient is being prepared to receive the graft as an implant. In the past, the graft has been stored in a wet towel or cloth that is wrapped around the graft. The towel is generally soaked in saline solution or other preservative liquid to prevent the graft from drying out while the implantation site in the patient is being prepared. Since the graft is generally totally wrapped up in the towel or cloth, on rare occasions, the graft has been mistakenly thrown away with the towel. Therefore, a need exists to provide a relatively safe and accessible site for storing a tendon graft while a patient is being prepared.

Yet, another aspect of such surgical procedures is that it is commonly necessary to accurately measure the length of a harvested graft, both before and after suturing. In the past, medical personnel have used a separate ruler or other measuring device to measure the length of a graft. The use of a separate measuring device can sometimes be inconvenient in an operating room in which a multitude of surgical instruments are present. It may be difficult for medical personnel to quickly locate a measuring device among the many surgical instruments. Therefore, a need existed to provide a measuring device in close proximity to the location at which a graft would be scraped and sutured.

SUMMARY OF THE INVENTION

The subject invention meets all of the needs discussed above. The subject invention can be briefly described as a device for tendon graft preparation that includes a pair of tension arms for positioning and tensioning a tendon graft. To that end, at least one of the tension arms is moveable in a horizontal plane to place tension on the graft. Both of the tension arms are moveable in a vertical plane to vertically position the graft. A pair of height-adjusting arms are provided for providing vertical movement of the tension arms. The device also includes a surface preparation area that is suitable for supporting a tendon when the tendon is being scraped or sutured. The surface preparation area is removably mounted on a base of the device. In one embodiment of the invention, the surface preparation area is a disposable. In other embodiments, the surface preparation area may be resterilized and reused.

In one embodiment, the device also includes a trough for storing a tendon after the tendon has been prepared for re-implantation into a patient. The device still further includes a means for measuring the length of a tendon graft.

BRIEF DESCRIPTION OF THE DRAWINGS

There follows a detailed description together with accompanying drawings of a preferred embodiment of the invention. However, it is to be understood that the invention is capable of numerous modifications and variations apparent to those skilled in the art that are within the spirit and scope of the invention.

DETAILED DESCRIPTION OF THE PREFERRED EMBODIMENT

Figure 4:
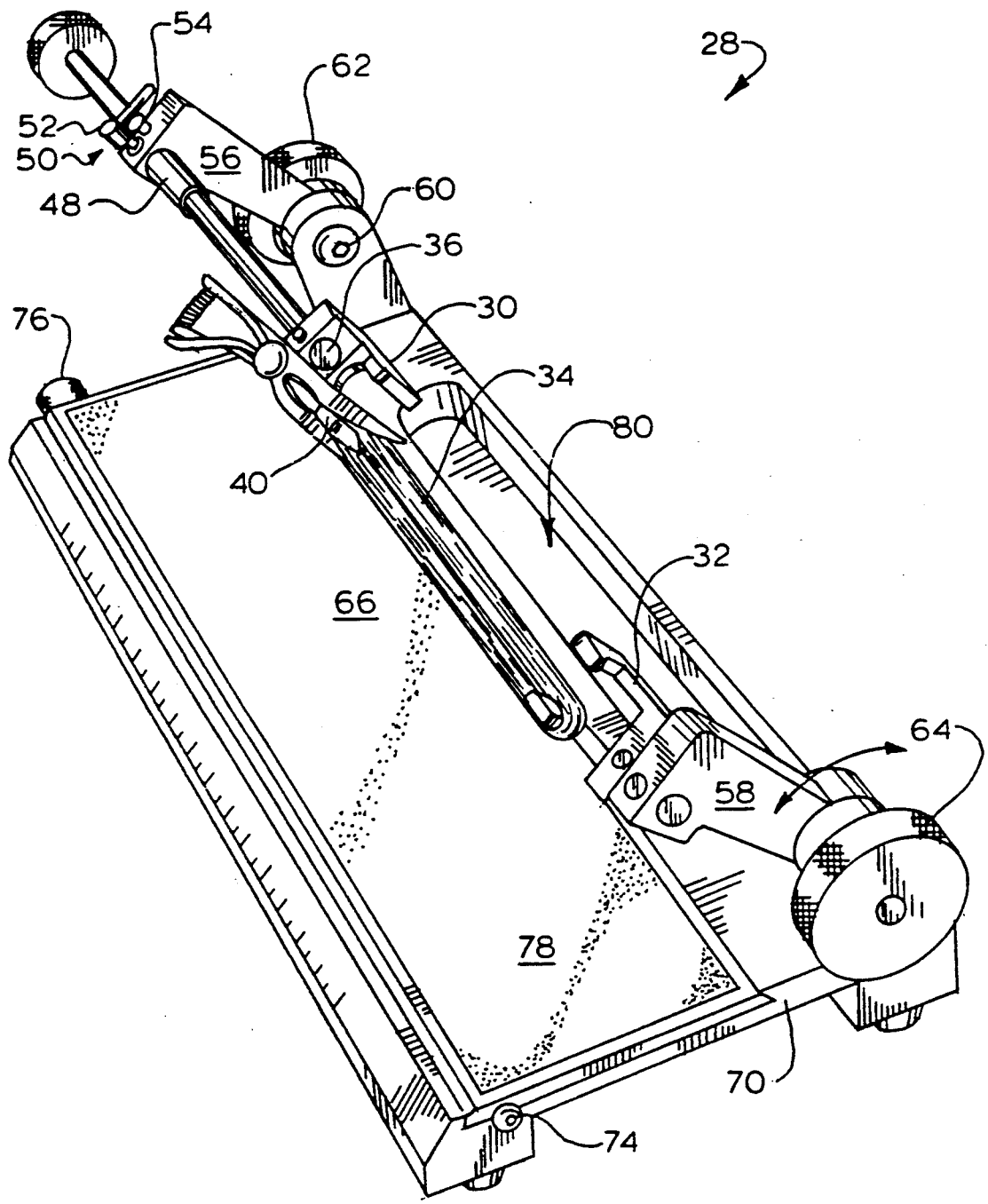
FIG. 4 is a perspective view of the preferred embodiment of the subject invention.

Refer now to FIG. 4 which is a perspective view of the preferred embodiment of the subject invention. As can be seen in the figure, the device 28 includes a pair of tension arms 30, 32. The tension arms are used to position and place tension on a tendon graft 34. At least one of the tension arms 30 is moveable in a horizontal plane to place tension on the graft 34. Both of the tension arms 30, 32 are moveable in a vertical plane to vertically position the graft. In the preferred embodiment of the invention, the tension arms 30, 32 are rotatable about a first central axis 36. As can be seen in the figure, a tendon 34 can be looped around one of the tension arms 32. The tension arm 32 may then be moved in a horizontal plane to produce tension on the tendon.

Figure 1:
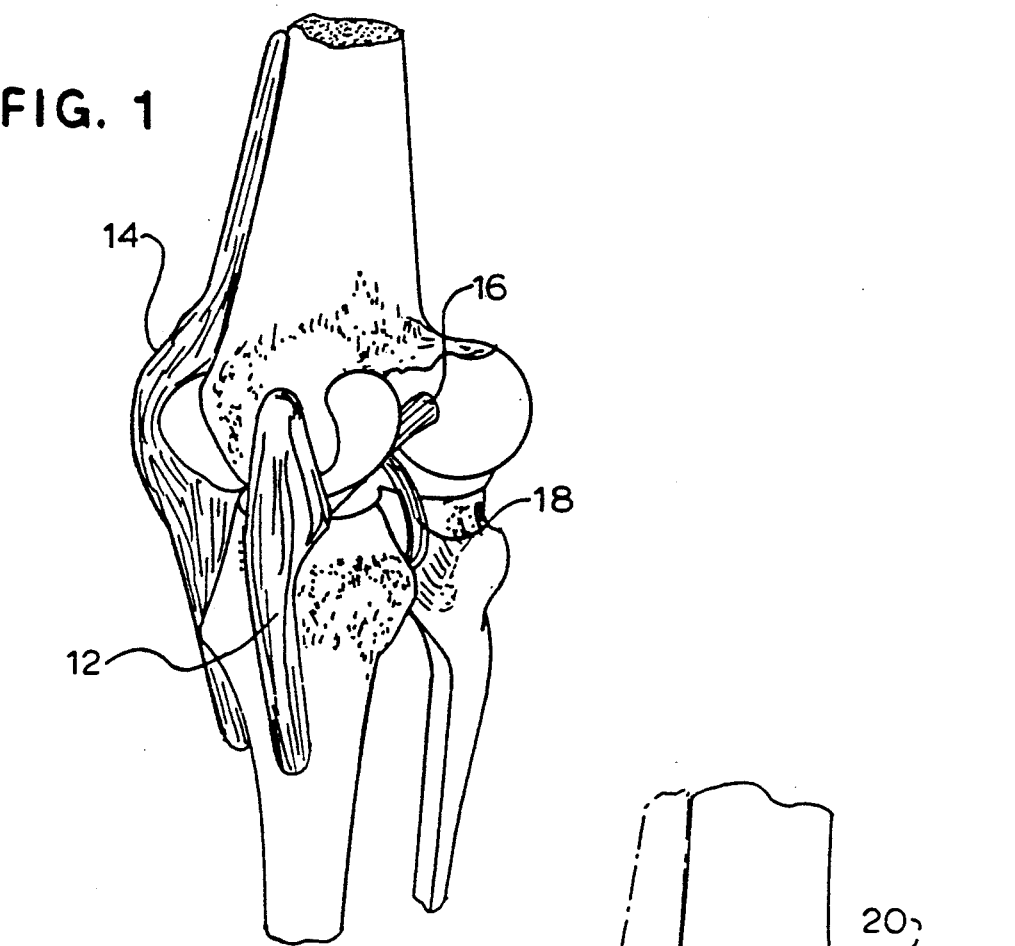
FIG. 1 is a perspective view of a patient's knee area illustrating the anterior and posterior ligaments as well as the mid-third patellar mid-section and the semitendinosus gracilis.
Figure 2:
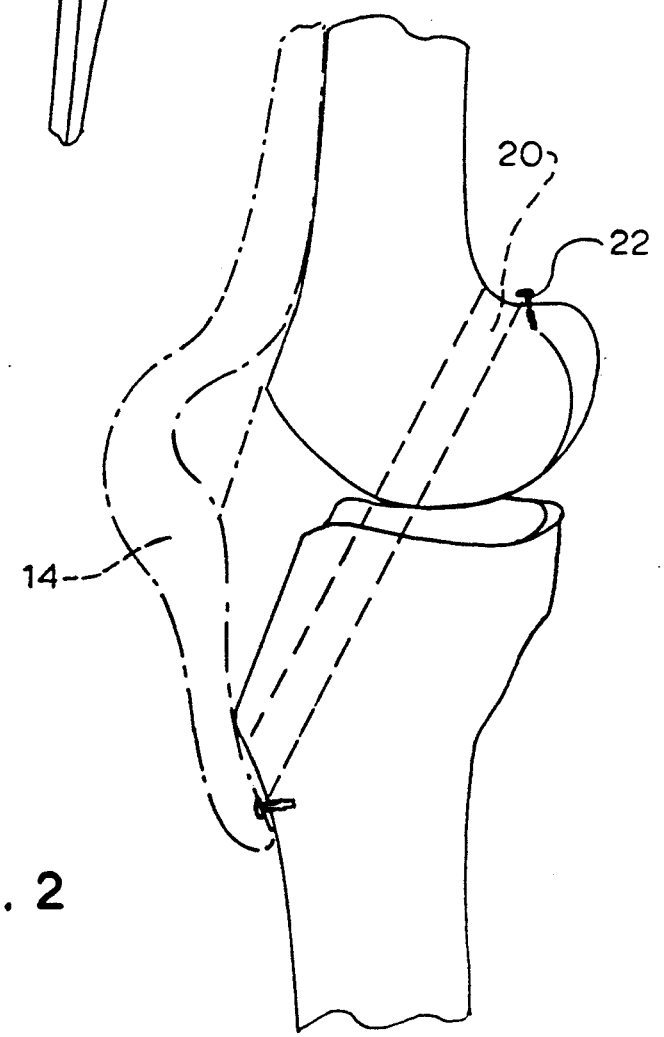
FIG. 2 is a perspective view of a patient's knee area illustrating a reconstructed tunnel configuration.
Figure 3:
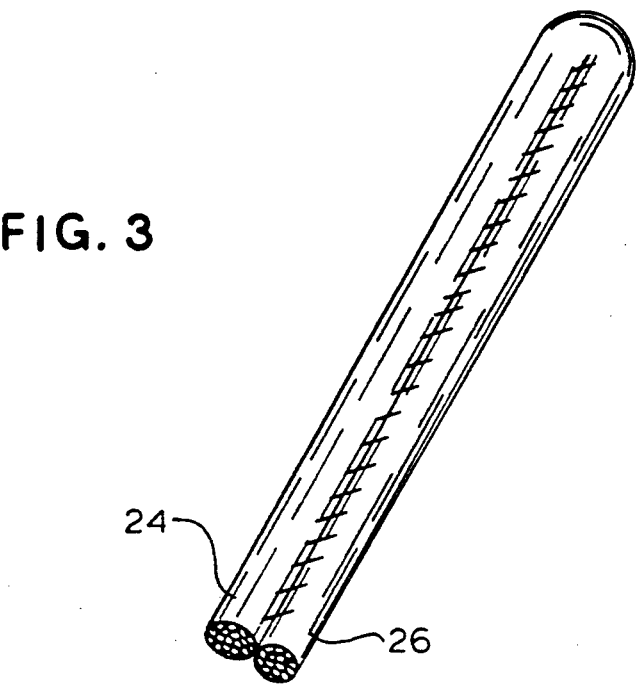
FIG. 3 is a perspective view of a tendon graft which has been looped and sutured.
Figure 5:
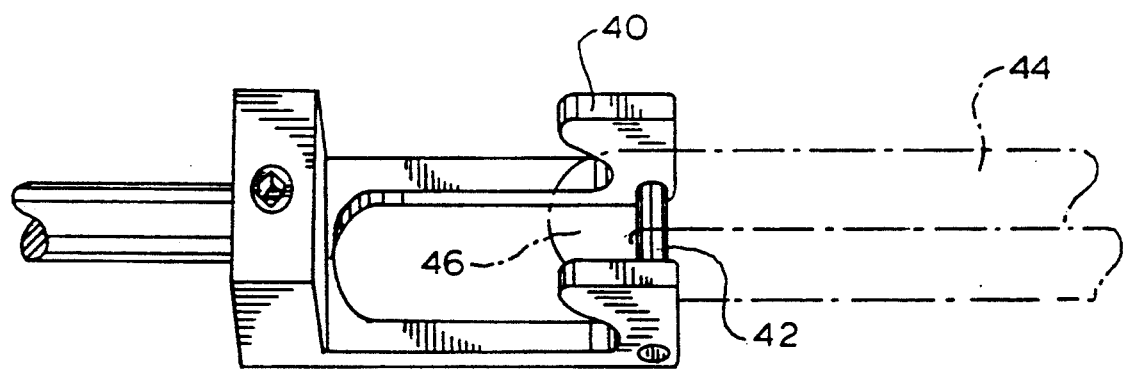
FIG. 5 is a side view of one embodiment of a tension arm.

In one embodiment of the invention, the tendon is maintained in the tension arms 30, 32 through the use of bulldog clamps which can be straddled over a pair of extension hooks 40 located on each tension arm. In another embodiment of the invention illustrated in FIG. 5, the hooks 40 of each tension arm include a means for receiving a pin 42. A tendon graft 44 may then be looped over the pin 42 to place one end 46 of the graft 44 under tension.

Refer once again to FIG. 4, as can be seen in this figure, at least one of the tension arms 30 can be moved horizontally through a sliding gate 48 and locked in position with a locking means 50. In the preferred embodiment, the locking means is a self-locking screw 52. When the screw is rotated in a clockwise direction, it will apply sufficient pressure to the tension arm 30 to lock the tension arm in a fixed horizontal position. When the screw 52 is rotated in a counter-clockwise direction, it will horizontally release the tension arm 30 to allow sliding movement of the arm through the locking gate 48. In a preferred embodiment of the invention, a fixation screw 54 is provided which will self lock the locking screw 52 to prevent accidental removal of the locking screw 52 from the device 28.

As can also be seen in FIG. 4, a pair of height-adjusting arms 56 and 58 are provided. The height-adjusting arms are attached to each one of the tension arms 30 and 32, respectively. Each of the height-adjusting arms 56, 58 are independently rotatable about a second central axis 60 to provide a means for adjusting the vertical position of each of the tension arms 30, 32. The vertical position of each height-adjusting arm can be fixed by rotating its respective adjusting knob 62, 64. The adjusting knobs serve to lock each of the height-adjusting arms in a fixed position.

Figure 6:
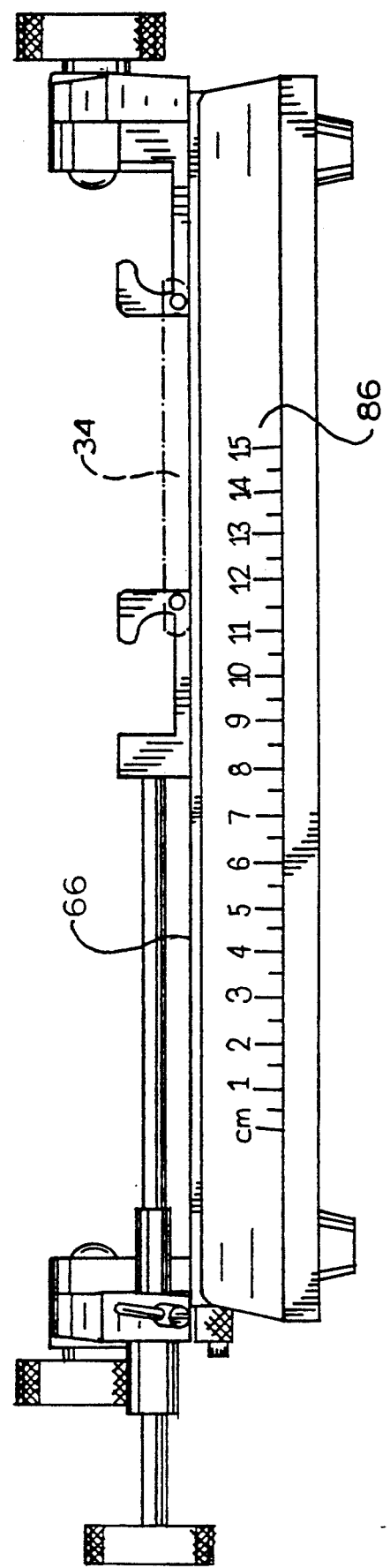
FIG. 6 is a perspective view of one embodiment of the invention in which a graft is located directly on a surface preparation area.

As can be seen in FIG. 4, in one embodiment of the invention, the height-adjusting arms can be positioned in an upper position in which a tendon graft 34 is suspended above a surface preparation area 66. In another embodiment of the invention as can be seen in FIG. 6, the tension arms can be positioned directly on the surface preparation area so that the surface preparation area 66 can provide support for the graft 34.

Figure 7:
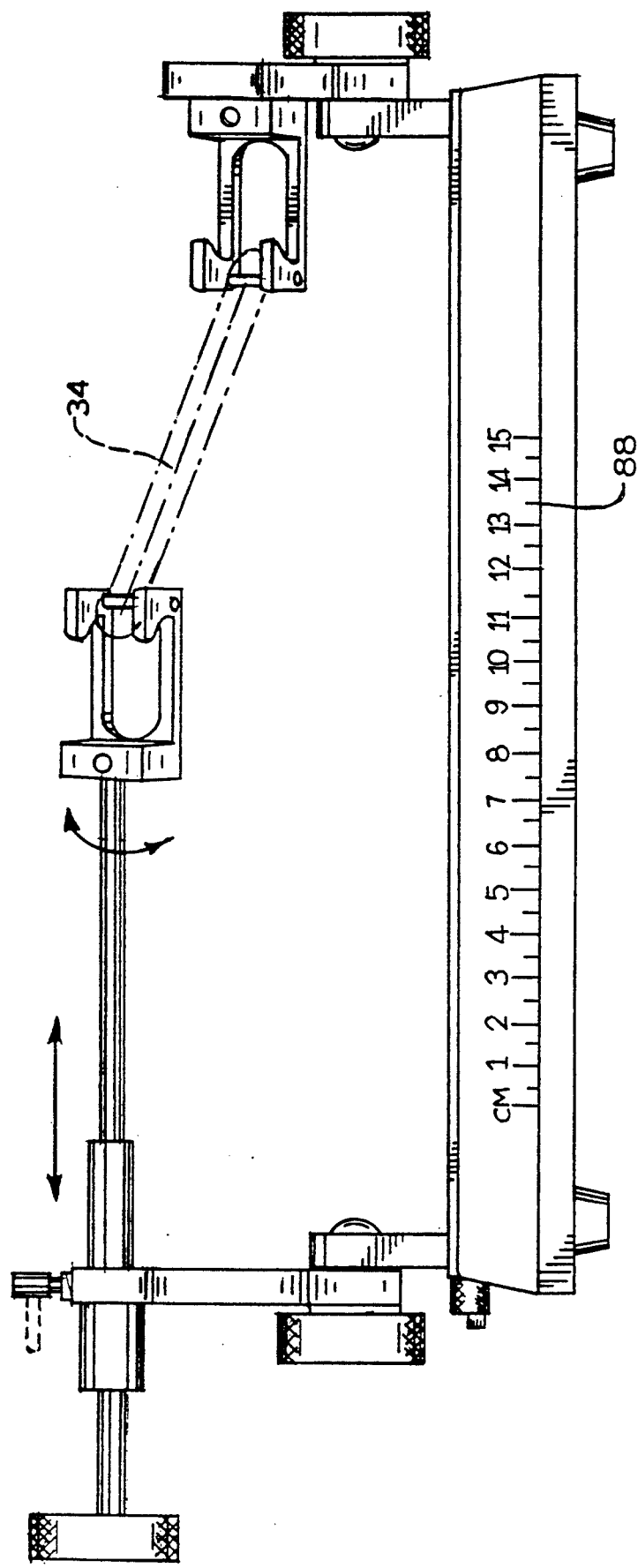
FIG. 7 is another embodiment of the invention in which a graft is suspended at an angle.

The ability to change the vertical position of each of the tension arms allows a doctor great flexibility when suturing a tendon graft. For instance, some doctors like to have a tendon graft supported by the surface preparation area during the suturing process. Other doctors prefer to have the tendon graft suspended as it is being sutured. In some instances, a doctor may prefer to have the graft positioned at a slant to enhance the angle at which a graft is being sutured together. In such cases, a doctor may position one of the tension arms directly on the surface preparation area and position the other of the tension arms well above the surface preparation area to provide the desired angle. This is illustrated in FIG. 7.

Figure 8:
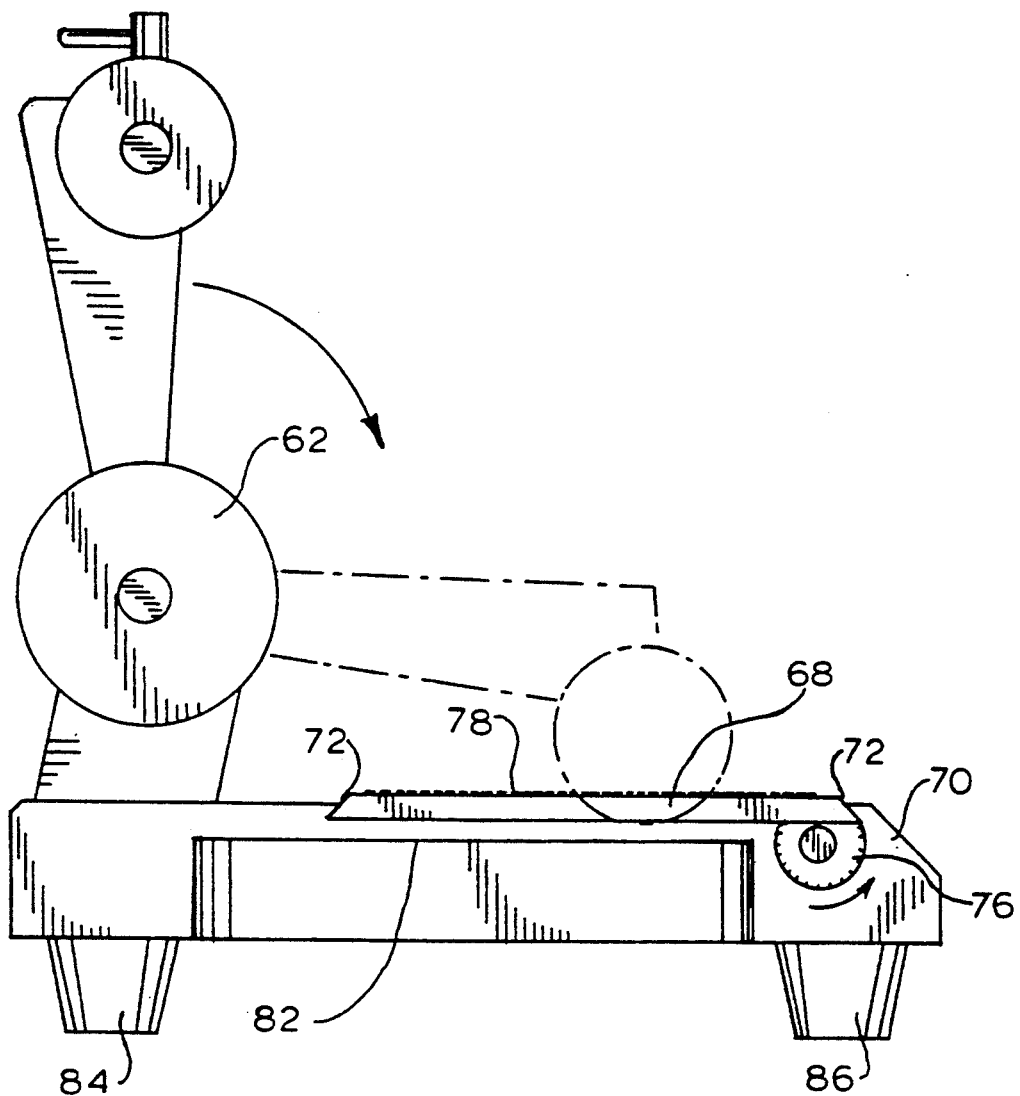
FIG. 8 is an end view of one embodiment of the invention.

As can be seen in FIG. 8, which is a side view of one embodiment of the invention, the surface preparation area is a separate sheet of material 68. The sheet 68 is removably mounted in a base 70 of the device. The base 70 includes dovetail groves 72 for receiving the sheet 68. One end of the base includes a permanent stop lock post 74 to prevent lateral movement of the sheet 68. The stoplock post 74 prevents the sheet 68 from extending beyond a first end of the base 70. The other end of the base 70 includes a releasable stoplock 76 to allow the sheet to be removed from the grove by sliding the sheet over the stoplock. The releasable stoplock 76 is rotatable from a first position that allows removal of the sheet to a second position which keeps the sheet in a locked position in the grove 72.

The surface preparation area can be either a disposable material or a reusable material. In one embodiment of the invention, the surface preparation area is formed of an ABS plastic which is not intended to be resterilized or reused. In another embodiment of the invention, the surface preparation area is formed from a stainless steel that can be resterilized and reused. In both embodiments, the surface preparation area includes an upper surface 78 which is sandblasted to provide a non-slip surface. This is very useful to a doctor when a tendon graft is placed on the surface to scrape away any "meaty" material on the graft.

As can also be seen in FIG. 4, the base 70 also includes a means for storing and preserving the tendon after the tendon has been prepared for re-implantation into a patient. In the preferred embodiment, the means includes a trough 80 in which the prepared tendon can be placed. The trough is deep enough to allow the tendon to be totally submerged in a preservative solution. Generally, the solution is a saline solution. However, other solutions may be used as desired by a physician.

Refer now to FIG. 8. Another feature of the subject invention is the inclusion of a pair of recessed gripping areas 82 (one shown) in which one gripping area 82 is located at each end of the base. The gripping area allows medical personnel to easily grasp the device to move it from one location to another. Also shown in FIG. 8 is a pair rubber stabilization feet 84, 86 which serve to position the base 70 in a fixed location on a table. A measuring means 88 is also provided on one side of the base to allow medical personnel to measure the length of a tendon graft. In the preferred embodiment, the means 88 is engraved on the side of the base.

While the invention has been described in detail and with reference to specific embodiments thereof, it will be apparent to those skilled in the art that various changes and modifications can be made therein without departing from the spirit and scope of the invention.

I claim:

1. A device for tendon graft preparation, comprising:
   a pair of tension arms for positioning and tensioning a tendon graft, at least one of said tension arms being movable in a horizontal plane to place tension on said graft, and both of said tension arms being movable in a vertical plane to position said graft;
   a pair of height-adjusting arms, each of said height-adjusting arms being attached to one of said tension arms, said height-adjusting arms being independently rotatable, from each other, about a central axis to provide a means for adjusting the vertical position of each of said tension arms;
   a base to which said height adjusting arms are pivotally mounted, said base being positionable on a table;
   a surface preparation area supported by said base, said surface preparation area being suitable for supporting said graft while said graft is being scraped or sutured; and
   said height adjusting arms being rotatable to position said tension arms and said graft in contact with said surface preparation area.

2. A device as recited in claim 1 wherein:
   each of said tension arms are rotatable about a central axis.

3. A device as recited in claim 2 wherein:
   each of said tension arms are rotatable about a central axis by 360 degrees.

4. A device as recited in claim 1, further comprising:
   horizontal locking means for locking in a fixed horizontal position any of said tension arms that are movable in a horizontal plane.

5. A device as recited in claim 4, wherein:
   said locking means further includes a self-locking screw that when rotated in a clockwise direction will lock said tension arm in a fixed horizontal position, and when rotated in a counter-clockwise direction will horizontally release said tension arm and said locking means further including means for self locking to prevent accidental removal of said screw from said device.

6. A device as recited in claim 1, wherein:
   said surface preparation area further includes a non-slip surface.

7. A device as recited in claim 1, wherein:
   said base comprises a means for removably mounting said surface preparation area.

8. A device as recited in claim 7, further comprising a pair of height-adjusting arms pivotally mounted on said base.

9. A device as recited in claim 7, wherein said base further includes:
   a trough for preserving said tendon after said tendon has been prepared for re-implantation into a patient, said trough being able to contain a preserving solution for soaking said tendon.

10. A device as recited in claim 7, wherein said base further includes measuring indicia for measuring the length of a tendon.

11. A device as recited in claim 7, wherein said base further includes:
    two recessed gripping areas for lifting a positioning said base, said gripping areas being positioned on opposite ends of said base.

12. A device as recited in claim 11, wherein said base further includes:
    gripping means for positioning said base on a table.

13. A device as recited in claim 7, wherein:
    said means for removably mounting said surface preparation area includes a dovetail grove for receiving said surface preparation area;
    said surface preparation area includes a sheet of material having a non-skid upper surface;
    means for locking said surface preparation area in a lateral position to prevent movement of said surface preparation area while a tendon is being scraped on said surface preparation area.

14. A device as recited in claim 13, wherein said locking means includes:
    a permanent stop lock post at a first end of said base to prevent said surface preparation area from sliding beyond said first end; and
    a releasable stop lock at a second end of said base to allow said surface preparation area to be slid out of said groove when said releasable stop lock is in a first position and to allow said surface preparation area to be locked in position in said groove when said releasable stop lock is in a second position.

15. A device as recited in claim 14, wherein said sheet is formed of a sterilizable material.

16. A device as recited in claim 15, wherein said sheet is formed of 316 stainless steel with a sand-blasted, non-skid surface.

17. A device as recited in claim 14, wherein said sheet is formed of a disposable material.

18. A device as recited in claim 17, wherein said sheet if formed of ABS plastic.

19. A device as recited in claim 1 further comprising:
    means for locking each of said height-adjusting arms in a fixed position.

20. A device as recited in claim 1, wherein at least one of said tension arms includes a means for looping a portion of a tendon about said tension arm.

21. A device as recited in claim 20, wherein:
    at least one of said tension arms includes a pair of hook-shaped extensions; and
    said looping means includes a pin removably mounted between said extensions.

22. A device as recited in claim 1 wherein:
    said tension arms and said height adjusting arms are rotatable 180 degrees about a horizontal axis to position said graft while maintaining tension on said graft.

* * * * *